United States Patent
Homma

(10) Patent No.: US 11,375,882 B2
(45) Date of Patent: Jul. 5, 2022

(54) ENDOSCOPE SYSTEM WHICH GENERATES AN IMAGE OF HIGH DYNAMIC RANGE

(71) Applicant: OLYMPUS CORPORATION, Hachioji (JP)

(72) Inventor: Hiroyuki Homma, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 397 days.

(21) Appl. No.: 16/702,289

(22) Filed: Dec. 3, 2019

(65) Prior Publication Data

US 2020/0138275 A1 May 7, 2020

Related U.S. Application Data

(63) Continuation of application No. PCT/JP2018/015261, filed on Apr. 11, 2018.

(30) Foreign Application Priority Data

Jun. 7, 2017 (JP) .............................. JP2017-112518

(51) Int. Cl.
*A61B 1/00* (2006.01)
*A61B 1/06* (2006.01)
(Continued)

(52) U.S. Cl.
CPC ...... *A61B 1/00163* (2013.01); *A61B 1/00188* (2013.01); *A61B 1/05* (2013.01);
(Continued)

(58) Field of Classification Search
None
See application file for complete search history.

(56) References Cited

U.S. PATENT DOCUMENTS 6,677,992 B1 * 1/2004 Matsumoto .......... H04N 5/2354
   348/E5.038
8,672,838 B2   3/2014 Mcdowall
(Continued)

FOREIGN PATENT DOCUMENTS

JP    H11155808 A    6/1999
JP    2004313523 A   11/2004
(Continued)

OTHER PUBLICATIONS

International Preliminary Report on Patentability (IPRP) (and English translation thereof) dated Dec. 19, 2019, Bsued in counterpart International Application No. PCT/JP2018/015261.
(Continued)

*Primary Examiner* — John P Leubecker
(74) *Attorney, Agent, or Firm* — Holtz, Holtz & Volek PC

(57) ABSTRACT

An endoscope system includes an illuminator configured to switch between a first illumination light and a second illumination light for which a ratio of a quantity of light is $1/\alpha$, an objective optical system, an image sensor, an optical path splitter which is disposed between the objective optical system and the image sensor, the optical path splitter has an optical path splitting surface, a first reflecting surface, and a second reflecting surface. A processor acquires for each of the first illumination light and the second illumination light, a first image pickup signal and a second image pickup signal, combines the first image pickup signal and the second image pickup signal for the first illumination light and the first image pickup signal and the second image pickup signal for the second illumination light, and generates an image of a high dynamic range. Here, $\alpha$ denotes a coefficient.

9 Claims, 7 Drawing Sheets

(51) Int. Cl.
  *G02B 27/12* (2006.01)
  *G06T 7/00* (2017.01)
  *A61B 1/05* (2006.01)

(52) U.S. Cl.
  CPC .......... *A61B 1/0661* (2013.01); *G02B 27/126* (2013.01); *G06T 7/0012* (2013.01); *G06T 2207/10028* (2013.01); *G06T 2207/10068* (2013.01); *G06T 2207/20208* (2013.01)

(56) References Cited

U.S. PATENT DOCUMENTS

| | | | |
|---|---|---|---|
| 8,684,914 | B2 | 4/2014 | Mcdowall et al. |
| 8,734,328 | B2 | 5/2014 | Mcdowall |
| 8,764,633 | B2 | 7/2014 | Mcdowall |
| 8,784,301 | B2 | 7/2014 | Mcdowall |
| 10,206,554 | B2 | 2/2019 | Mizuno |
| 2013/0038689 | A1 | 2/2013 | Mcdowall |
| 2013/0041215 | A1 | 2/2013 | Mcdowall |
| 2013/0041216 | A1* | 2/2013 | McDowall ......... A61B 1/00193 600/109 |
| 2013/0041221 | A1 | 2/2013 | Mcdowall et al. |
| 2013/0041226 | A1 | 2/2013 | Mcdowall |
| 2014/0176692 | A1* | 6/2014 | Tsuyuki ............. A61B 1/00009 348/71 |
| 2015/0092035 | A1 | 4/2015 | Yamamoto et al. |
| 2017/0049306 | A1* | 2/2017 | Katakura .......... A61B 1/00096 |
| 2017/0086649 | A1* | 3/2017 | Mizuno ................ A61B 1/0002 |
| 2019/0219831 | A1* | 7/2019 | Duckett ............... A61B 1/0019 |
| 2020/0081235 | A1* | 3/2020 | Takahashi ........... G02B 21/361 |

FOREIGN PATENT DOCUMENTS

| | | |
|---|---|---|
| JP | 2005176940 A | 7/2005 |
| JP | 2007274285 A | 10/2007 |
| JP | 2013255655 A | 12/2013 |
| JP | 2014524290 A | 9/2014 |
| JP | 6017735 B2 | 10/2016 |
| WO | 2013025530 A1 | 2/2013 |
| WO | 2016059983 A1 | 4/2016 |
| WO | 2017073292 A1 | 5/2017 |

OTHER PUBLICATIONS

International Search Report (ISR) dated Jul. 17, 2018 issued in International Application No. PCT/JP2018/015261.
Written Opinion dated Jul. 17, 2018 issued in International Application No. PCT/JP2018/015261.

* cited by examiner

ENDOSCOPE SYSTEM WHICH GENERATES AN IMAGE OF HIGH DYNAMIC RANGE

CROSS-REFERENCE TO RELATED APPLICATION

The present application is a continuation application of PCT/JP2018/015261 filed on Apr. 11, 2018, which is based upon and claims the benefit of priority from Japanese Patent Application No. 2017-112518 filed on Jun. 7, 2017; the entire contents of which are incorporated herein by reference.

BACKGROUND

Technical Field

The disclosure relates to an endoscope system.

Description of the Related Art

In smart phones and the like, a technology called as high dynamic range for photographing an object in which a difference in bright and dark of luminance is large has hitherto been known. The high dynamic range is a technology for reducing saturated white and blocked up shadows in an object image. In the high dynamic range, a bright image photographed in a long exposure time and a dark image photographed in a short exposure time, are combined. Accordingly, it is possible to achieve an image of the high dynamic range.

The high dynamic range is applicable not only to still images but also to movable image generation. For example, in Japanese Patent Application Laid-open Publication No. 2007-274285, an arrangement for achieving a moving image of high dynamic range by using an attenuator which periodically changes light incident on an image sensor has been disclosed.

Moreover, in Japanese Patent Application Laid-open Publication No. 2005-176940 and Japanese Patent No. 6017735 Publication, an arrangement in which, in an optical system for endoscope, an optical image is split into two optical images by a beam splitter, and the two optical images split are formed on an image pickup surface of one image sensor has been disclosed.

In Japanese Patent Application Laid-open Publication No. 2013-255655, an arrangement which enables to acquire an image having image characteristics to be acquired without a need of complicated image processing by illuminating an object with the most suitable illuminating characteristics according to image characteristics of an image to be acquired has been disclosed.

In Japanese Patent Application Laid-open Publication No. 2004-313523, an arrangement having two light receivers, which improves the dynamic range has been disclosed.

SUMMARY

An endoscope system according to at least some embodiments includes;
an illuminator configured to switch between a first illumination light and a second illumination light for which a ratio of a quantity of light is $1/\alpha$,
an objective optical system,
an image sensor,
an optical path splitter disposed between the objective optical system and the image sensor, the optical path splitter has (i) an optical path splitting surface for splitting alight beam from an objective optical system into a light beam reflected and a light beam transmitted, the optical path splitter has (ii) a first reflecting surface having a first reflectance, the first reflecting surface reflects a light beam that has been reflected at the optical path splitting surface, and the optical path splitter has (iii) a second reflecting surface having a second reflectance differing from the first reflectance, and the second reflecting surface reflects a light beam that has been transmitted through the optical path splitting surface, and
a processor configured to:
acquire for each of the first illumination light and the second illumination light, a first image pickup signal formed as an image in a first area of the image sensor by a light beam reflected at the first reflecting surface and a second image pickup signal formed as an image in a second area which is different from the first area of the image sensor, by a light beam reflected at the second reflecting surface,
combine the first image pickup signal and the second image pickup signal for the first illumination light, and the first image pickup signal and the second image pickup signal for the second illumination light, and
generate an image of a high dynamic range, and
here, $\alpha$ denotes a coefficient.

DETAILED DESCRIPTION

An endoscope system according to an embodiment will be described below in detail by referring to the accompanying diagrams. However, the present disclosure is not restricted to the embodiment described below.

Figure 1:
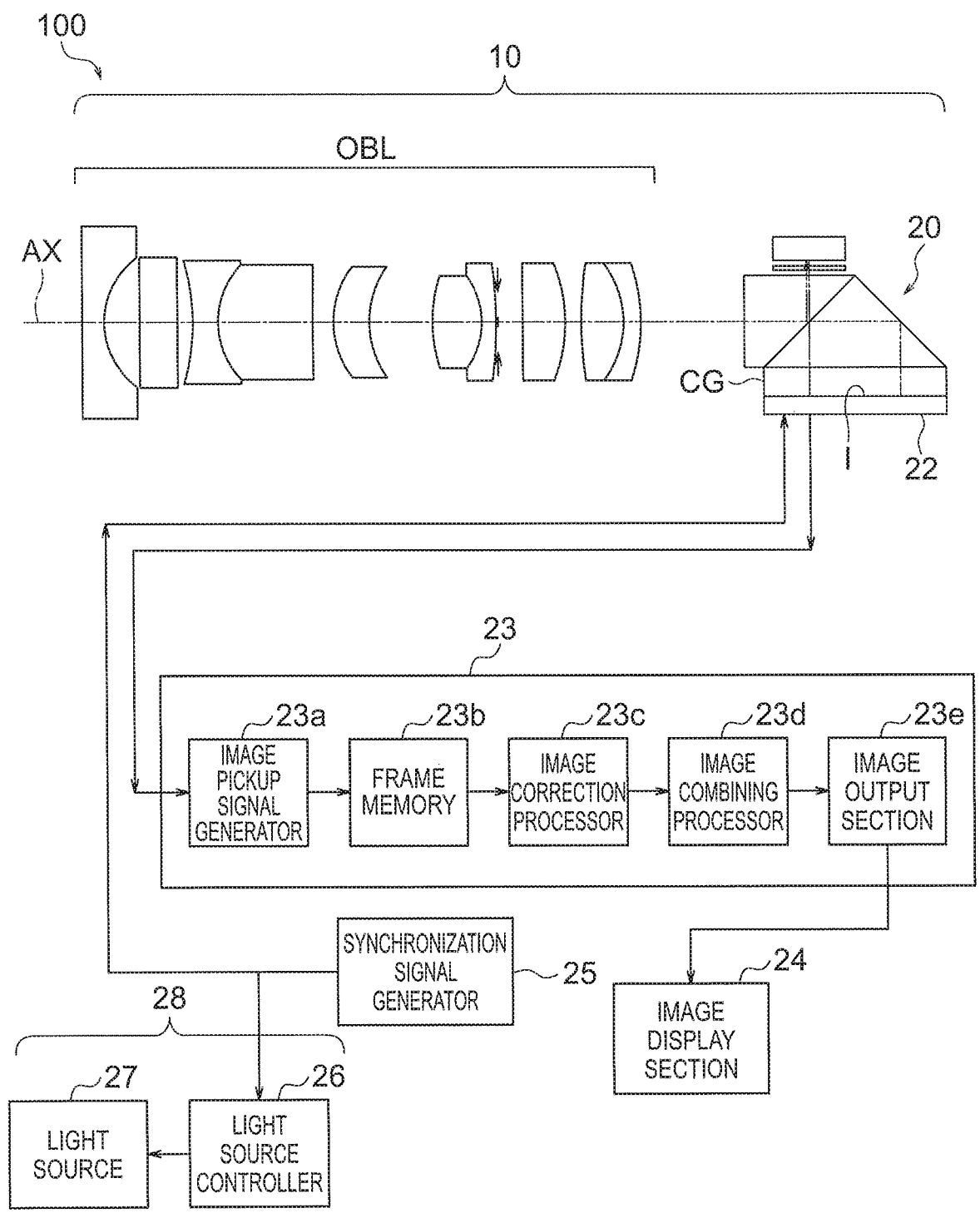
FIG. 1 is a diagram showing a schematic arrangement of an endoscope system according to an embodiment.

FIG. 1 is a diagram showing a schematic arrangement of an endoscope system 100 according to the embodiment. The endoscope system 100 includes an image pickup optical system 10 which acquires simultaneously two optical images of different brightness for the same object, an illuminator 28 which switches between a first illumination light quantity and a second illumination light quantity by synchronizing with timings at which first frame data and second frame data are picked up alternately, and a processor 23 which generates an image of high dynamic range by two images of different brightness acquired from the first frame data and two images of different brightness acquired from the second frame data, and when a ratio of brightness of the two images having different brightness is α, a ratio of the first illumination light quantity and the second illumination light quantity are 1/α.

In FIG. 1, a synchronization signal generator 25 outputs a synchronization signal to an image sensor 22 and a light-source controller 26. A light source 27 irradiates illumination light of illumination necessary at the time of picking up a first frame. Moreover, the light source 27 irradiates illumination light of illumination necessary at the time of picking up a second frame. Accordingly, it is possible to switch between the first illumination light quantity and the second illumination light quantity. The light-source controller 26 and the light source 27 form the illuminator 28.

Accordingly, in the first frame data, it is possible to acquire two optical images of EXP×α and EXP×1. In the second frame data, it is possible to acquire two optical images of EXP×1 and EXP×1/α.

Moreover, by combining the optical images of two frames, it is possible to achieve an image of high dynamic range.

Figure 2:
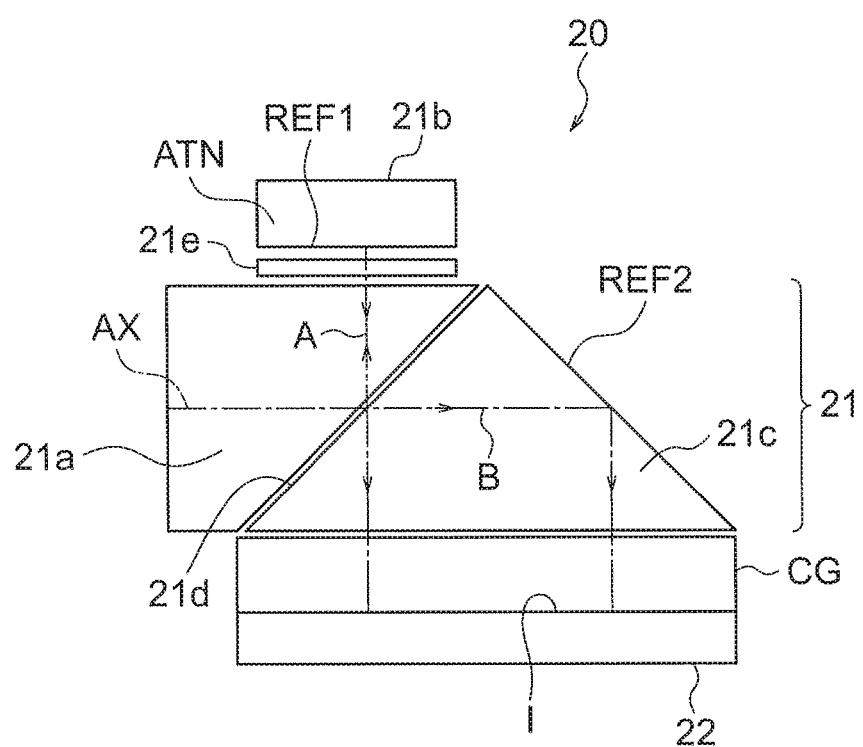
FIG. 2 is a schematic block diagram of an optical path splitter and an image sensor in the embodiment.

FIG. 2 is a schematic block diagram of an optical path splitter 20 and the image sensor 22. According to a preferable aspect of the present embodiment, the image pickup optical system 10 includes an objective optical system OBL for forming a light beam from an object, into an image, the one image sensor 22 which is disposed near an image forming position of the objective optical system OBL, and the optical path splitter 20 which is disposed between the objective optical system OBL and the image sensor 22, and the optical path splitter 20 has an optical path spitting surface 21d for splitting a light beam from the objective optical system OBL into two light beams which are a light beam reflected and a light beam transmitted.

The optical path splitter 20 has a first reflecting surface REF1 for reflecting upon bending a light beam reflected at the optical path splitting surface 21d, and the optical path splitter 20 has a second reflecting surface REF2 for reflecting light transmitted through the optical path splitting surface 21d.

A first optical image is formed in a first area 22a of the image sensor 22, by a light beam reflected at the first reflecting surface REF1 via the optical path splitting surface 21d. A second optical image is formed in a second area 22b (FIG. 3A and FIG. 3B) which is different from the first area 22a, of the image sensor 22, by a light beam reflected at the second reflecting surface REF2. An image pickup signal generator 23a (FIG. 1) carries out opto-electric conversion of the first optical image and the second optical image, and outputs as a first image pickup signal and a second image pickup signal respectively.

Here, a reflectance of the first reflecting surface REF1 and a reflectance of the second reflecting surface REF2 differ mutually, and one reflecting surface has a reflecting mirror of a reflectance r1 and the other reflecting surface has a reflecting mirror of a reflectance r1×α, and the following conditional expressions (1) and (2) are satisfied.

$$80 \leq r1 \leq 99 \quad (1)$$

$$0.2 \leq \alpha \leq 0.7 \quad (2)$$

where, r1 denotes a reflectance (%) for a visible light region.

Here, for the reflectance r1, the visible light region refers to an average value of a wavelength region from 400 nm to 700 nm. For instance, as a representative value of the reflectance r1, it is desirable to use a value when the wavelength is 550 nm.

A lower limit value of conditional expression (1) is a value in a case of an aluminized reflecting surface. Moreover, an upper limit value of conditional expression (1) is a value in a case of a silver-deposited reflecting surface. Due to the optical path splitter, the brightness is reduced to half. Therefore, of the two images having different brightness, the bright image is required to be of a bright optical system. When a value falls below the lower limit value of conditional expression (1), there is a lack of brightness.

Furthermore, when a value falls below a lower limit value of conditional expression (2), an effect of widening the dynamic range is reduced. When an upper limit value of conditional expression (2) is exceeded, dark noise due to the image sensor becomes susceptible to be remarkable in a dark image out of the two images.

An arrangement of the optical path splitter 20 will be described further by referring to FIG. 2. The optical path splitter 20 of the present embodiment is an example in which a light ray is split by using polarization of light.

Light emerged from the objective optical system OBL is incident on the optical path splitter 20. The optical path splitter 20 includes a polarization beam splitter 21 which splits an object image into two optical images, and the image sensor 22 which acquires two images by picking up the two optical images.

The polarization beam splitter 21, as shown in FIG. 2, includes an object-side prism 21a, an image-side prism 21c, a mirror 21b, and a λ/4 plate 21e. Both the object-side prism 21a and the image-side prism 21c have an optical path splitting surface which is inclined at 45 degrees with respect to an optical axis AX.

A polarization splitting film 21d is formed on the optical path splitting surface of the object-side prism 21a. Moreover, the object-side prism 21a and the image-side prism 21c form the polarization beam splitter 21 by bringing the respective optical path splitting surfaces in contact via the polarization splitting film 21d.

Moreover, the mirror 21b is provided near an edge surface of the object-side prism 21a via the λ/4 plate 21e. The image sensor 22 is attached to an edge surface of the image-side prism 21c via a cover glass CG. Here, I is an image formation surface (image pickup surface).

An object image from the objective optical system OBL is spit into a P-polarized component (light transmitted) and an S-polarized component (light reflected) by the polarization splitting film 21d provided to the optical path spitting surface of the object-side prism 21a, is split into two optical images which are an optical image on a reflected-light side an optical image on a transmitted-light side.

The optical image of the S-polarized component is reflected toward a facing surface with respect to the image sensor 22 at the polarization splitting film 21 and follows an optical path A, and after being transmitted through the λ/4 plate 21e, is reflected at the mirror 21b, and is returned toward the image sensor 22. The optical image which is returned has a direction of polarization turned by 90° by being transmitted once again through the λ/4 plate 21e, and is transmitted through the polarization splitting film 21d and is formed on the image sensor 22.

The optical image of the P-polarized component is transmitted through the polarization splitting film 21d and follows an optical path B, and upon being reflected by a mirror surface of the image-side prism 21c which is returned perpendicularly toward the image sensor 22, provided on an opposite side of the optical path splitting surface, and is formed on the image sensor 22.

In such manner, the object-side prism 21a and the image-side prism 21c spit the object image into two optical images of different brightness.

Figure 3A:
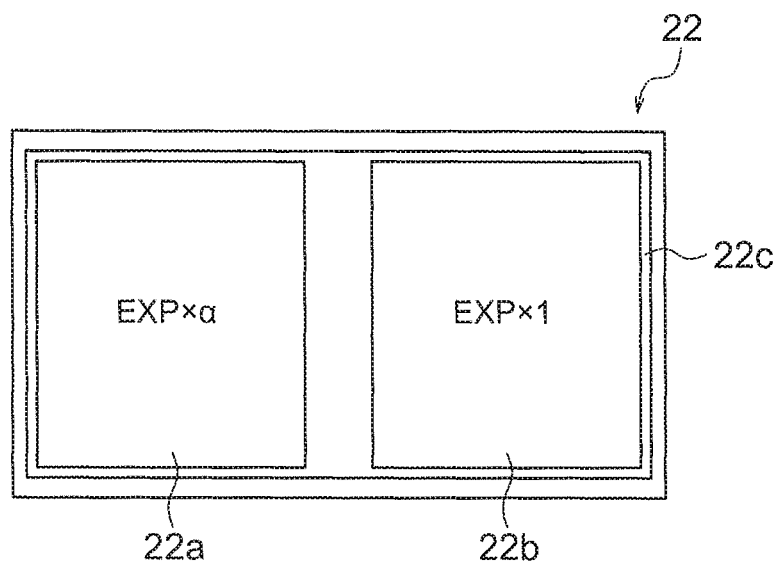
FIG. 3A is a diagram showing an image sensor in the endoscope system according to the embodiment and FIG. 3B is another diagram showing an image sensor in the endoscope system according to the embodiment.
Figure 3B:
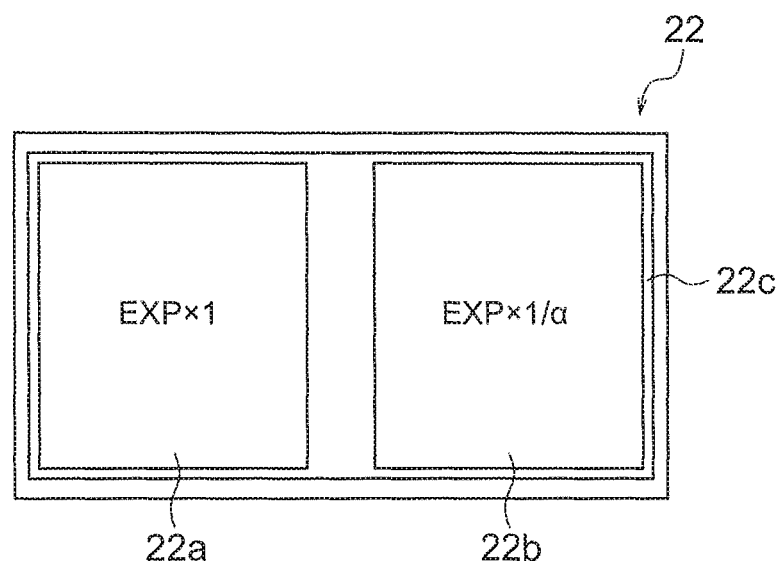

FIG. 3A is a diagram showing the first frame data of the image sensor 22 in the endoscope system 100 according to the present embodiment. FIG. 3B is a diagram showing the second frame data of the image sensor 22 in the endoscope system 100 according to the present embodiment.

The image sensor 22, as shown in each of FIG. 3A and FIG. 3B, is provided with two light receiving areas (effective pixel areas) 22a and 22b in an overall pixel area of the image sensor 22 for picking up images by receiving separately the two optical images having different brightness.

Here, as mentioned above, the reflectance of the first reflecting surface REF1 and the reflectance of the second reflecting surface REF2 differ mutually, and one reflecting surface has a reflecting mirror of reflectance r1 (%), and the other reflecting surface has a reflecting mirror of reflectance r1 (%)×α.

The two optical images of different brightness, in FIG. 3A, are two optical images of brightness EXP×α and EXP×1 when the reference brightness is EXP. Moreover, the two optical images of different brightness, in FIG. 3B, are two optical images of brightness EXP×1 and EXP×1/α.

The light receiving areas 22a and 22b are disposed to coincide with the respective image forming surfaces of these optical images in order to pick up the two optical images.

Moreover, a correction pixel area 22c for correcting a geometrical shift of the optical image divided into two is provided around the light receiving areas 22a and 22b. The abovementioned geometrical shift of the optical images is to be eliminated by suppressing a manufacturing error in the correction pixel area, and carrying out correction by image processing in an image correction processor 23c (FIG. 1) that will be described later.

Moreover, according to a preferable aspect of the present embodiment, it is desirable to install an attenuator ATN (FIG. 2) on a rear-surface side of a reflecting surface having a low reflectance out of the first reflecting surface REF1 and the second reflecting surface REF2 having different reflectance.

It is possible to use an absorbing filter such as an ND (neutral density) filter, a light shielding member, a black cloth or paint for the attenuator ATN. Moreover, the attenuation may be carried out by rotating the λ/4 plate 21e. Furthermore, the attenuator may be formed by mirror coating a dielectric film on the absorbing filter.

As mentioned above, in the present embodiment, the optical path separating surface is the polarization splitting film 21d (polarization beam splitter surface), and has the λ/4 plate 21e for changing a phase of a light beam reflected at the polarization beam splitter 21 between the polarization beam splitter 21 and the first reflecting surface REF1, and the light beam reflected at the first reflecting surface REF1 is formed as an image in the first area 22a on the image sensor 22 via the λ/4 plate 21e and the polarization beam splitter 21. Accordingly, it is possible to split a light beam while using even more effective light quantity.

The processor 23 (FIG. 1) will be described below.

The processor 23 includes the image pickup signal generator 23a which reads each image according to the two optical images of different brightness picked up by the image sensor 22, a frame memory 23b which stores the two images read by the image pickup signal generator 23a, the image correction processor 23c which carries out image correction, image combining processor 23d which carries out image combining processing of combining the two images that have been corrected, and an image output section 23e.

The image correction processor 23c carries out correction of the two images such that relative positions, angle, and magnification of the corresponding images of the two optical images formed on the light receiving areas 22a and 22b respectively of the image sensor 22 become substantially same.

In a case of forming images on the image sensor by splitting an object image into two, geometrical difference arises in some cases. In other words, there are cases in which there occurs a relative shift in magnification, shift in position, and a shift in angle or in other words, a direction of rotation of the optical images formed in the light receiving areas 22a and 22b respectively (FIG. 3A and FIG. 3B) of the image sensor 22.

It is difficult to eliminate completely these differences at the time of manufacturing, and when an amount of these shifts becomes large, the combined image becomes a double image or there is an unusual unevenness in brightness. Therefore, the abovementioned geometrical difference and brightness difference are to be corrected in the image correction processor 23c.

Moreover, the processor 23 carries out post processing such as color matrix processing, outline enhancement, and gamma correction of one image combined by the image combining processor 23d. The image output section 23e outputs the image subjected to the post processing. The image output from the image output section 23e is output to an image display section 24.

Examples will be described below.

Example 1

Figure 4:
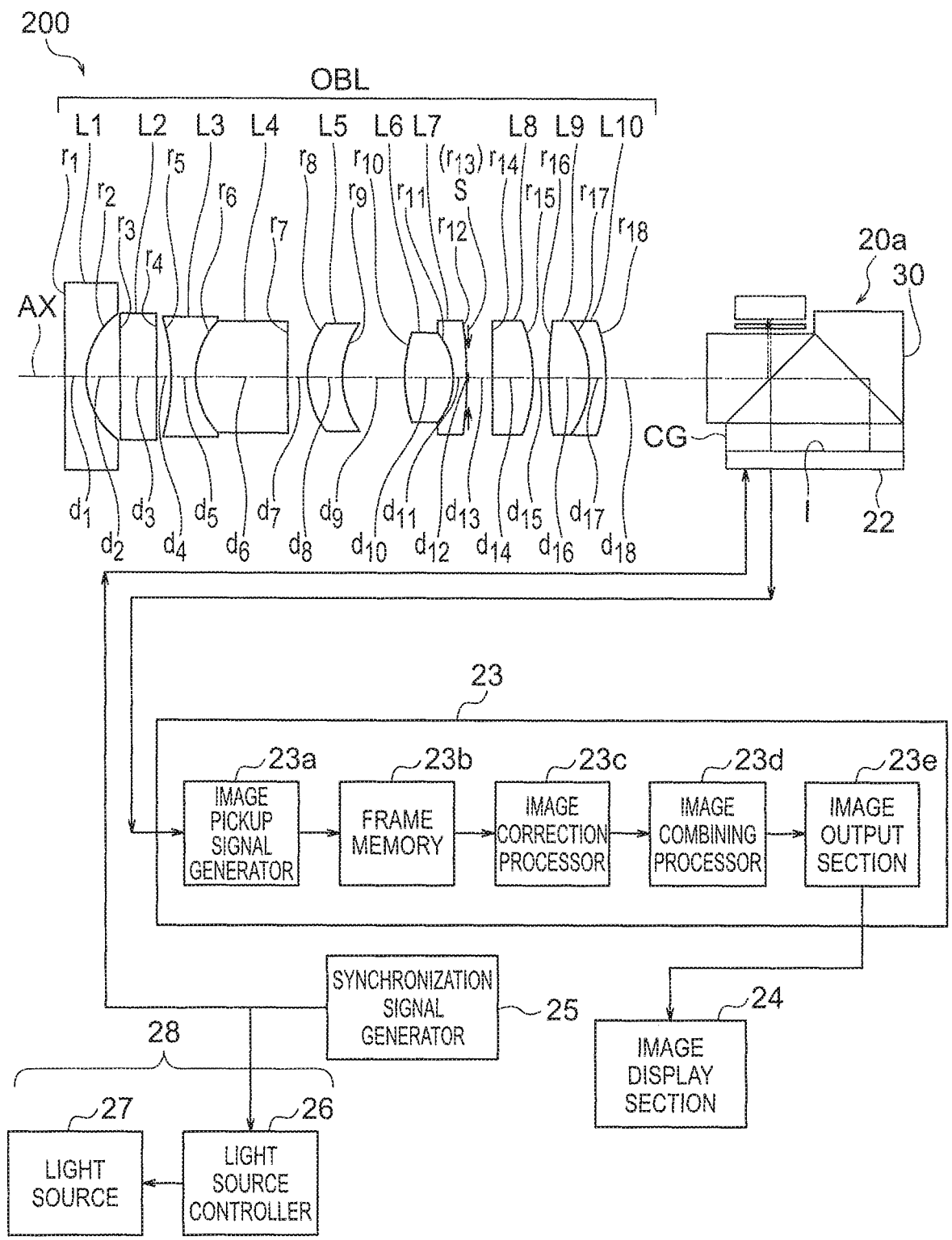
FIG. 4 is a diagram showing a schematic arrangement of an endoscope system according to an example 1.

Next, an objective optical system OBL in an endoscope system 200 according to an example 1 will be described below. FIG. 4 is a diagram showing a schematic arrangement of the endoscope system 200.

The objective optical system OBL includes in order from an object side, a planoconcave negative lens L1 having a flat surface directed toward the object side, a plane parallel plate L2, a biconcave negative lens L3, a positive meniscus lens L4 having a convex surface directed toward an image side, a positive meniscus lens L5 having a convex surface directed toward the object side, a biconvex positive lens L6, a negative meniscus lens L7 having a convex surface directed toward the image side, an aperture stop S, a biconvex positive lens L8, a biconvex positive lens L9, and a negative meniscus lens L10 having a convex surface directed toward the image side.

Here, the biconcave negative lens L3 and the positive meniscus lens L4 are cemented. The biconvex positive lens L6 and the negative meniscus lens L7 are cemented. The biconvex positive lens L9 and the negative meniscus lens L10 are cemented.

An optical path splitter 20a is disposed on the image side of the objective optical system OBL. An optical path is bent in a prism inside the optical path splitter 20a. The plane parallel plate L2 is a filter having a coating applied thereto for cutting off specific wavelengths such as 1060 nm of YAG (yttrium aluminum garnet) laser, 810 nm of semiconductor laser, or an infrared region. Here, I is an image forming surface (image pickup surface).

Numerical data for each example is shown below. Regarding symbols, r denotes a radius of curvature of each lens surface, d denotes a distance between two lens surfaces, nd denotes a refractive index for a d-line of each lens, vd denotes Abbe's number for each lens, FNO denotes an F-number, and ω denotes a half angle of view. Moreover, back focus fb is a distance from an optical surface nearest to image up to a paraxial image plane, expressed upon air conversion. An overall length is a length obtained by adding the back focus to a distance (not subjected to air conversion) from a lens surface nearest to object up to an optical surface nearest to image. A stop is the aperture stop.

Example 1

Unit mm

Surface data

| Surface no. | r | d | nd | vd |
|---|---|---|---|---|
| 1 | ∞ | 0.49 | 1.88300 | 40.76 |
| 2 | 1.812 | 0.79 | | |
| 3 | ∞ | 0.84 | 1.52100 | 65.12 |
| 4 | ∞ | 0.34 | | |
| 5 | −4.881 | 0.56 | 1.88300 | 40.76 |
| 6 | 1.866 | 2.13 | 1.84666 | 23.78 |
| 7 | 77.332 | Variable | | |
| 8 | 2.010 | 0.81 | 1.48749 | 70.23 |
| 9 | 2.149 | Variable | | |
| 10 | 3.354 | 1.13 | 1.64769 | 33.79 |
| 11 | −1.665 | 0.32 | 2.00330 | 28.27 |
| 12 | −9.987 | 0.04 | | |
| 13 (Stop) | ∞ | 0.56 | | |
| 14 | 512.363 | 0.95 | 1.69895 | 30.13 |
| 15 | −3.552 | 0.36 | | |
| 16 | 9.128 | 0.94 | 1.48749 | 70.23 |
| 17 | −2.180 | 0.39 | 1.92286 | 18.90 |
| 18 | −4.093 | 4.59 | | |
| 19 (Image pickup surface) | ∞ | | | |

Various data

| | |
|---|---|
| Focal length | 1.00 |
| FNO. | 3.58 |
| 2ω | 144.9 |
| fb (in air) | 4.59 |
| Total length (in air) | 17.15 |
| d7 | 0.47 |
| d9 | 1.43 |

Figure 5:
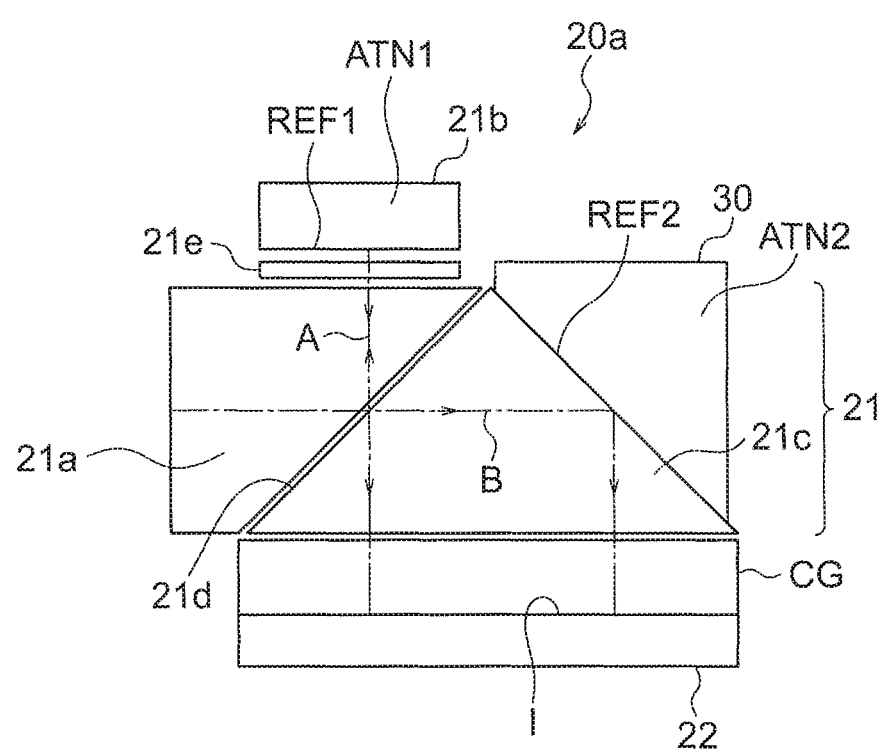
FIG. 5 is a schematic block diagram of an optical path splitter and an image sensor in the endoscope system according to the example 1.

FIG. 5 is a schematic block diagram of the optical path splitter 20a and an image sensor 22 in the endoscope system 200 according to the example 1. Same reference numerals are assigned to components that are same as in the abovementioned embodiment, and repetitive description thereof is omitted.

A polarization prism 30 is cemented to an inclined surface of an image-side prism 21c of the optical path splitter 20a. The polarization prism 30 has a function of an attenuator ATN2. Accordingly, it is possible to reduce stray light due to reflection at a mechanical member.

Example 2

Figure 6:
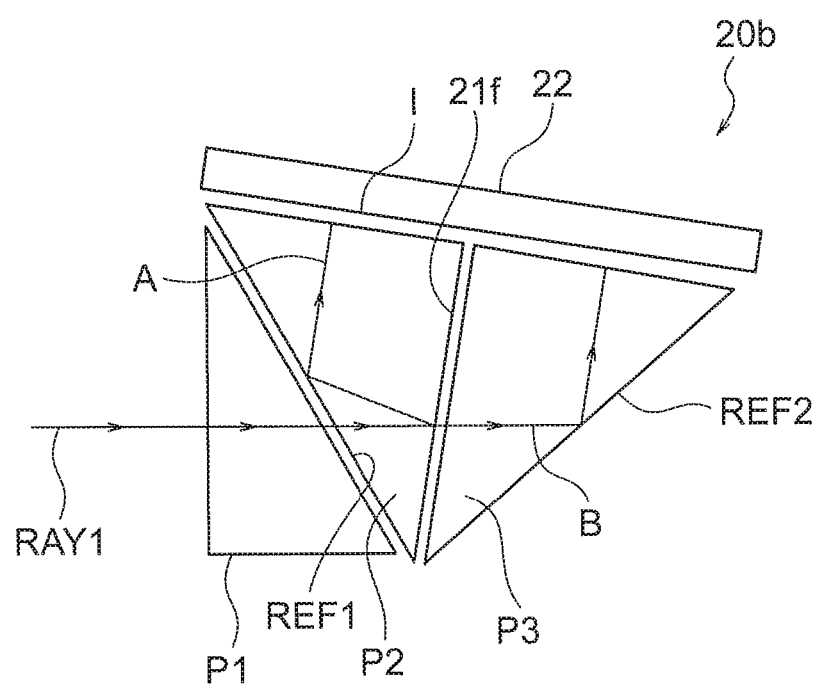
FIG. 6 is a schematic block diagram of an optical path splitter and an image sensor in an endoscope system according to an example 2.

FIG. 6 is a schematic block diagram of an optical path splitter 20b and an image sensor 22 in an endoscope system 200 according to an example 2. Same reference numerals are assigned to components that are same as in the abovementioned embodiment, and repetitive description thereof is omitted. An objective optical system OBL is same as the objective optical system OBL in the example 1.

The optical path splitter 20b includes (consists of) three right-angle prisms P1, P2, and P3, inclined surfaces of the right-angle prisms P1 and P2 are disposed leaving a gap between inclined surfaces, and the right-angle prisms P2 and P3 are cemented. A light beam split into two optical paths, an optical path A and an optical path B, by a half mirror 21f (an image-plane side of the right-angle prism P2) is incident on the image sensor 22 by a total reflection at inclined surfaces of the right-angle prism P2 and P3 respectively. In such manner, without using polarization, it is possible to acquire the abovementioned two images of different brightness by splitting the intensity.

Modified Example

A modified example is an arrangement in which the high dynamic range as mentioned above has been achieved, and which enables to make a depth of field large. An apparatus arrangement is same as the arrangement shown in FIG. 1 and FIG. 2. However, a process flow of optical images acquired differs from that in the abovementioned embodiment.

An object-side prism 21a and an image-side prism 21c are disposed such that an optical path length of a reflected-light side becomes shorter (smaller) than an optical path length (path length in glass) of a transmitted-light side reaching an image sensor 22 in the object-side prism 21a, in order to be able to split an object image into two optical images of different focusing position.

Light receiving areas 22a and 22b are disposed to coincide with an image forming surface of these optical images respectively in order to pick up the two optical images. Moreover, in the image sensor 22, a focusing position for the light receiving area 22a with respect to the light receiving area 22b is shifted relatively toward a near-point side, and a focusing position for the light receiving area 22b with respect to the light receiving area 22a is shifted relatively toward a far-point side. Accordingly, an arrangement is made to form the two optical images of different focus on two light receiving surfaces of the image sensor 22.

An arrangement may be made such that by making a refractive index of a glass of both the object-side prism 21a and the image-side prism 21c different, the focusing positions with respect to the light receiving areas 22a and 22b are shifted relatively by changing an optical path length reaching the image sensor 22.

The image combining processor 23d, in addition to having the function of the abovementioned high dynamic range, generates a combined image by selecting images having relatively high contrast. In other words, the image combining processor 23d compares a contrast in each of the spatially same pixel areas of two images, and by selecting a pixel area for which the contrast is relatively high, generates a combined image as one image combined from the two images.

An image output section 23e outputs an image subjected to post image processing. The image output from the image output section 23e is output to an image display section 24.

Accordingly, it is possible to acquire images for two optical images of different focus, and to achieve a combined depth of field by combining these images by the image combining processor 23d. A distant observation is suitable for screening by taking a long shot of a wide range in endoscopy, and a proximity observation is suitable for observing details of a lesion, and for diagnosis.

Figure 7A:
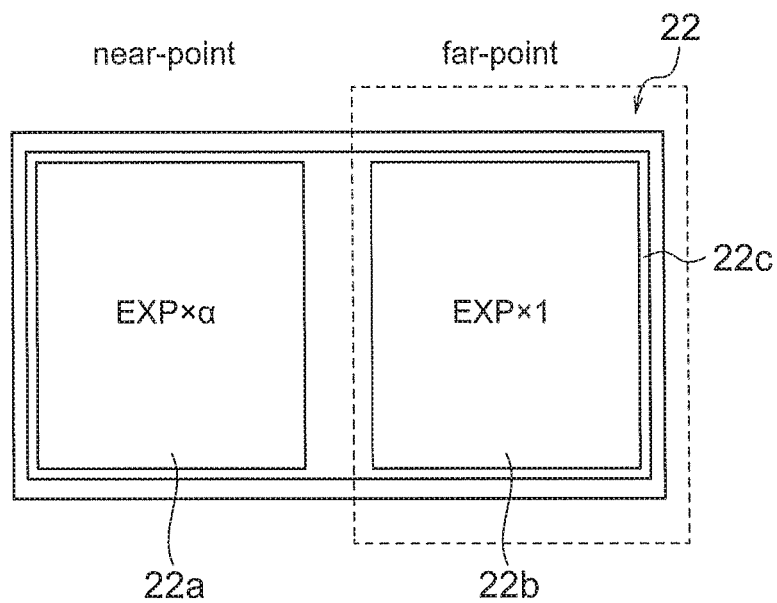
FIGS. 7A and 7B are diagrams illustrating how a depth of field is made large in an endoscope system according to a modified example.
Figure 7B:
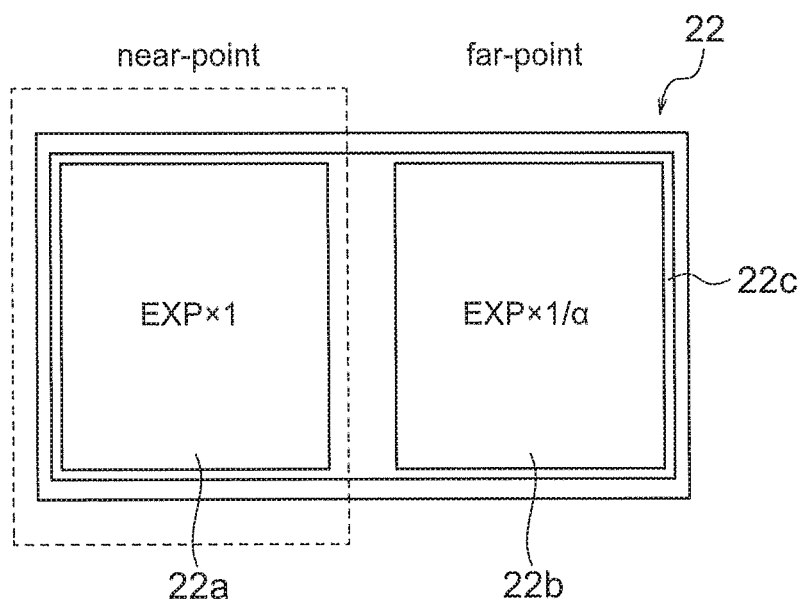

The image sensor 22, as shown in FIG. 7A and FIG. 7B, picks up by receiving separately the two images having different focusing positions. In this case, a brightness of an image surrounded by dashed lines in first frame data of FIG.

7A and a brightness of an image surrounded by dashed lines in second frame data of FIG. 7B are same.

Here, of the near-point side and the far-point side, it is preferable to make a dark side the near-point and a bright side the far-point. The reason is, the near-point side being brighter than the far-point side, information of EXP×1/α is not necessary anymore, and the far-point side being darker than the near-point side, information of EXP×α is not necessary anymore.

By making such arrangement, it is possible to widen the depth of field without degrading a resolution even when an image sensor in which the number of pixels is made even larger is used, while achieving the high dynamic range.

The abovementioned endoscope system may satisfy the plurality of arrangements simultaneously. Doing so is preferable for achieving a favorable endoscope system. Moreover, a combination of the preferable arrangements is arbitrary. Furthermore, for each conditional expression, only an upper limit value or a lower limit value of a further restricted numerical range of conditional expressions may be restricted.

Various embodiments of the present disclosure have been described above. However, the present disclosure is not restricted to the embodiments described above, and embodiments in which the arrangements of the embodiments described above are combined appropriately without departing from the scope of the present disclosure are also in the scope of the present disclosure.

Note

A disclosure having the following arrangements is derived from the examples described above.

Appended Mode 1

An endoscope system comprising:
an image pickup optical system which acquires simultaneously two optical images of different brightness, for the same object; and
an illuminator configured to switch between a first illumination light quantity and a second illumination light quantity by synchronizing with timings at which first frame data and second frame data are picked up alternately, wherein
the endoscope system generates an image of even higher dynamic range by two images of different brightness acquired from first frame data and two images of different brightness acquired from second frame data, and
when a ratio of brightness of the two images of different brightness is a, a ratio of the first illumination light quantity and the second illumination light quantity is 1/α.

Appended Mode 2

The endoscope system according to appended mode 1, further comprising:
an attenuator which is disposed on a rear-surface side of a reflecting surface having a low reflectance out of the first reflecting surface and the second reflecting surface having different reflectance, and which causes the reflectance of the first reflecting surface and the reflectance of the second reflecting surface to differ, and two images having different brightness are formed by the first reflecting surface and the second reflecting surface, wherein
the attenuator is any one of an absorbing filter, a dielectric multilayer film, and a black member As described heretofore, the present disclosure is useful for an endoscope system which is small in size and which enables to acquire an image with a wide dynamic range, and particularly a moving image with a wide dynamic range.

The present disclosure shows an effect that is possible to provide an endoscope system which is small in size and which enables to acquire an image with a wide dynamic range, and particularly, a moving image with a wide dynamic range.

What is claimed is:

1. An endoscope system, comprising:
an illuminator configured to switch between a first illumination light and a second illumination light for which a ratio of a quantity of light is 1/α, where α denotes a coefficient;
an objective optical system;
an image sensor;
an optical path splitter which is disposed between the objective optical system and the image sensor,
the optical path splitter including:
(i) an optical path splitting surface for splitting a light beam from the objective optical system into a light beam reflected and a light beam transmitted,
(ii) a first reflecting surface having a first reflectance, the first reflecting surface reflecting the light beam that has been reflected at the optical path splitting surface, and
(iii) a second reflecting surface having a second reflectance differing from the first reflectance, the second reflecting surface reflecting the light beam that has been transmitted through the optical path splitting surface; and
a processor configured to:
acquire, for each of the first illumination light and the second illumination light, a first image pickup signal formed as an image in a first area of the image sensor by a light beam reflected at the first reflecting surface and a second image pickup signal formed as an image in a second area of the image sensor, which is different from the first area, by a light beam reflected at the second reflecting surface,
combine the first image pickup signal and the second image pickup signal for the first illumination light and the first image pickup signal and the second image pickup signal for the second illumination light, and
generate an image of a high dynamic range.

2. The endoscope system according to claim 1, wherein:
the first reflecting surface has a reflecting mirror for which the first reflectance is r1,
the second reflecting surface has a reflecting mirror for which the second reflectance is r1×α, and
the endoscope system satisfies the following conditional expressions (1) and (2):

$$80 \leq r1 \leq 99 \quad (1)$$

$$0.2 \leq \alpha \leq 0.7 \quad (2)$$

where,
r1 denotes a reflectance (%) for a visible light region.

3. The endoscope system according to claim 1, wherein an attenuator is installed on a rear-surface side of a reflecting surface with a low reflectance from among the first reflecting surface and the second reflecting surface.

4. The endoscope system according to claim 1, wherein:
the optical path splitting surface comprises a polarization beam splitter, and has a λ/4 plate for changing a phase of a light beam reflected at the polarization beam splitter, between the polarization beam splitter and the first reflecting surface, and a light beam reflected at the first reflecting surface is formed as an image in the first area of the image sensor via the λ/4 plate and the polarization beam splitter.

5. The endoscope system according to claim 1, wherein:
the optical path splitter includes a first prism, a second prism, and a third prism in order from an object side toward an image side, and a half mirror is formed on a surface on a third-prism side of the second prism.

6. The endoscope system according to claim 5, wherein a light beam reflected at the half mirror is formed as an image in the first area, and a light beam transmitted through the half mirror is formed as an image in the second area.

7. The endoscope system according to claim 1, wherein:
a focusing position of the first area is shifted relatively toward a near point with respect to a focusing position of the second area, and the processor, in an area corresponding to the first image pickup signal and the second image pickup signal, combines an area of a relatively higher contrast, and generates an image of a high dynamic range and a large depth of field.

8. The endoscope system according to claim 7, wherein from among the first area and the second area, a dark area is shifted toward a near-point side and a bright area is shifted toward a far-point side.

9. The endoscope system according to claim 1, wherein
the optical path splitter includes a first prism and a second prism having mutually different refractive indices, in order from an object side toward an image side, the first image pickup signal and the second image pickup signal have different focusing positions due to a difference in the refractive index of the first prism and the refractive index of the second prism, and the processor, in an area corresponding to the first image pickup signal and an area corresponding to the second image pickup signal, combines an area of a relatively higher contrast, and generates an image of a high dynamic range and a large depth of field.

* * * * *